United States Patent [19]
Bryant et al.

[11] Patent Number: 5,649,931
[45] Date of Patent: Jul. 22, 1997

[54] ORTHOPAEDIC APPARATUS FOR DRIVING AND/OR REMOVING A BONE SCREW

[75] Inventors: Mark A. Bryant, Auburn; John E. Meyers, Columbia City, both of Ind.

[73] Assignee: Zimmer, Inc., Warsaw, Ind.

[21] Appl. No.: 586,103

[22] Filed: Jan. 16, 1996

[51] Int. Cl.⁶ ................................ A61B 17/88
[52] U.S. Cl. ........................ 606/104; 81/453
[58] Field of Search .............. 606/73, 99, 104; 81/451, 452, 453, 455

[56] References Cited

U.S. PATENT DOCUMENTS

| | | | |
|---|---|---|---|
| D. 290,399 | 6/1987 | Kitchens | D24/26 |
| D. 353,001 | 11/1994 | Petersen | D24/142 |
| 2,370,407 | 2/1945 | McCartney | 81/453 |
| 3,208,450 | 9/1965 | Abelson | 128/83 |
| 3,334,624 | 8/1967 | Schneider et al. | 128/92 |
| 3,626,935 | 12/1971 | Pollock et al. | 128/83 |
| 4,140,111 | 2/1979 | Morill | 128/92 E |
| 4,188,701 | 2/1980 | Lugwig | 29/275 |
| 4,263,903 | 4/1981 | Griggs | 128/92 B |
| 4,359,906 | 11/1982 | Cordey | 73/862.23 |
| 4,389,913 | 6/1983 | Drouin et al. | 81/53.2 |
| 4,423,721 | 1/1984 | Otte et al. | 128/92 EC |
| 4,438,769 | 3/1984 | Pratt et al. | 128/334 R |
| 4,531,517 | 7/1985 | Forte et al. | 128/92 EC |
| 4,592,346 | 6/1986 | Jurgutis | 128/92 B |
| 4,776,328 | 10/1988 | Frey et al. | 128/92 VT |
| 4,838,264 | 6/1989 | Bremer et al. | 128/303 B |
| 4,858,601 | 8/1989 | Glisson | 128/92 R |
| 4,901,712 | 2/1990 | Voegeli et al. | 606/75 |
| 4,903,691 | 2/1990 | Heinl | 606/70 |
| 4,911,154 | 3/1990 | Vickers | 606/104 |
| 4,963,144 | 10/1990 | Huene | 606/73 |
| 4,981,481 | 1/1991 | Kranz et al. | 606/62 |
| 4,995,810 | 2/1991 | Söderberg | 433/141 |
| 5,084,053 | 1/1992 | Ender | 606/104 |
| 5,139,499 | 8/1992 | Small et al. | 606/73 |
| 5,354,292 | 10/1994 | Braeuer et al. | 606/1 |
| 5,391,181 | 2/1995 | Johnson et al. | 606/207 |

OTHER PUBLICATIONS

Zimmer literature—Knee Systems, pp. A172.A173, ©1993.
Zimmer literature—Haig Nail, PP. B30; Kirschner Wires, Accessories, pp. B86; Other Instruments, pp. B102. ©1987.
Zimmer literature—Kirschner wire accessories, pp. B6; Alphabetical index; Jun. 1978.

*Primary Examiner*—Michael Buiz
*Assistant Examiner*—David O. Reip
*Attorney, Agent, or Firm*—Margaret L. Geringer

[57] ABSTRACT

The invention is directed to an orthopaedic apparatus 10 for at least one of removing and driving an elongated fixation member 12 having an enlarged head 22. The orthopaedic apparatus 10 includes a hollow, elongated body 14 having an open end 26 for receiving the enlarged head 22 therein. The body 14 further has a deflectable portion 28 at the open end. A shaft 16 is disposed within the body, and has a distal end 34 disposed substantially adjacent to the body open end. The distal end 34 has an exterior configuration which is adapted to mate with the enlarged head. The deflectable portion is configured to impart a radially inward force around the enlarged head and the shaft is configured to impart an axial compression force on the enlarged head, thereby locking the elongated fixation member relative to the orthopaedic apparatus.

10 Claims, 2 Drawing Sheets

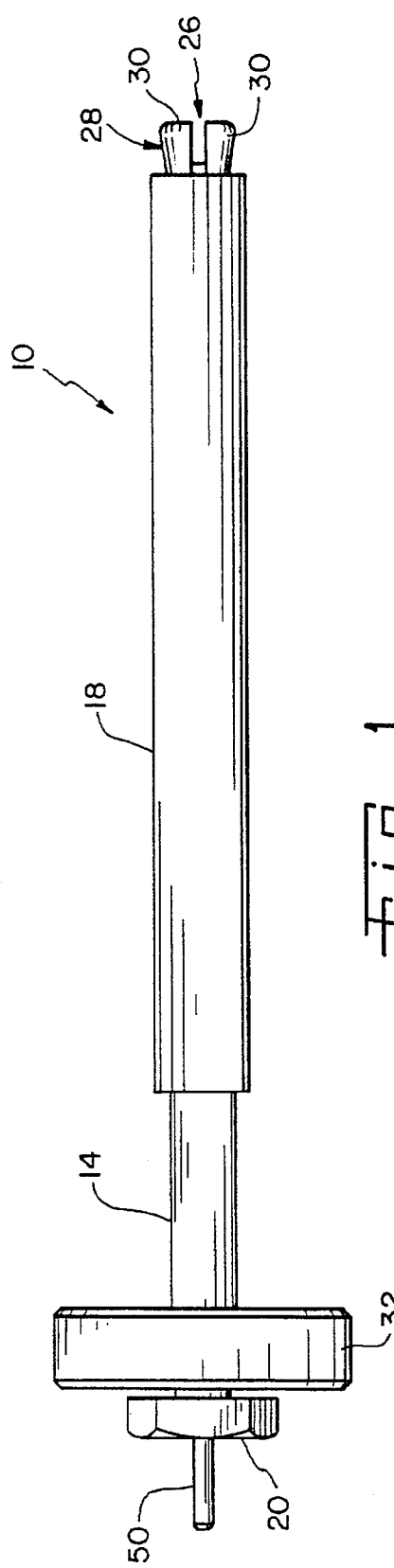
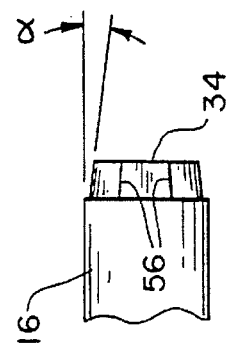
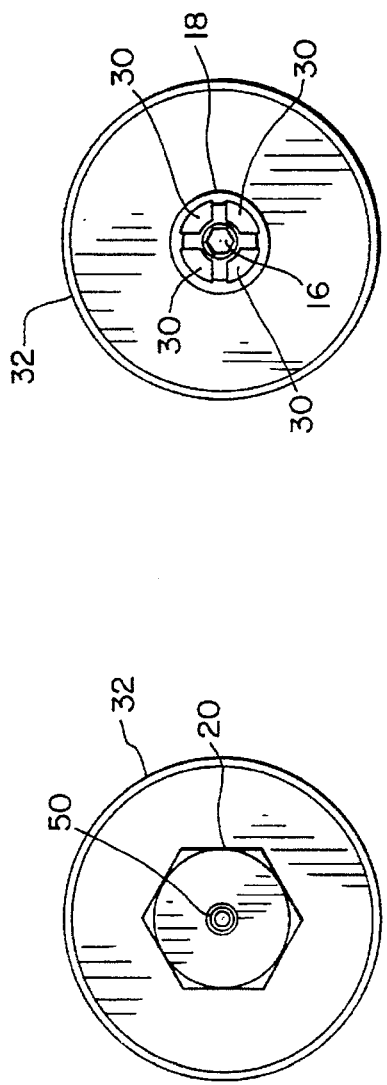

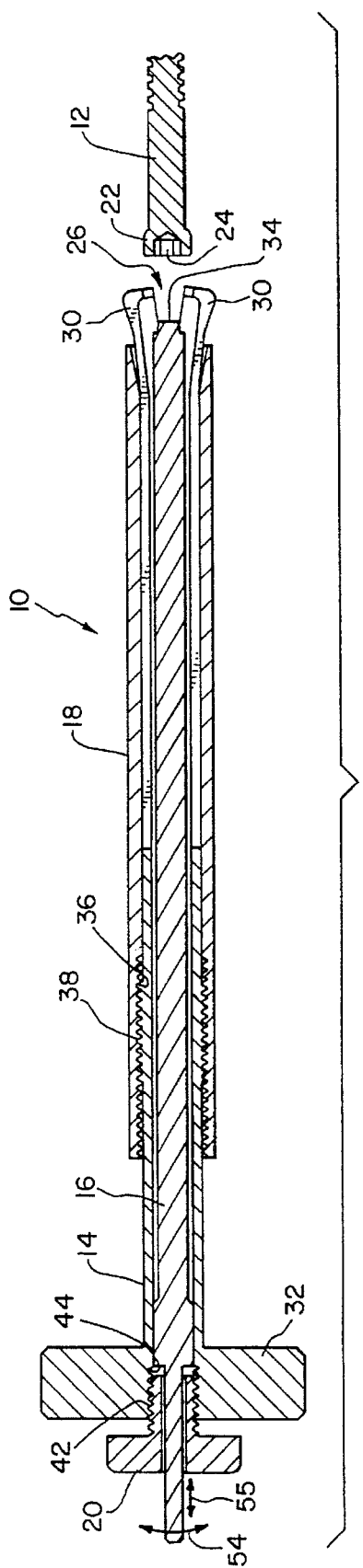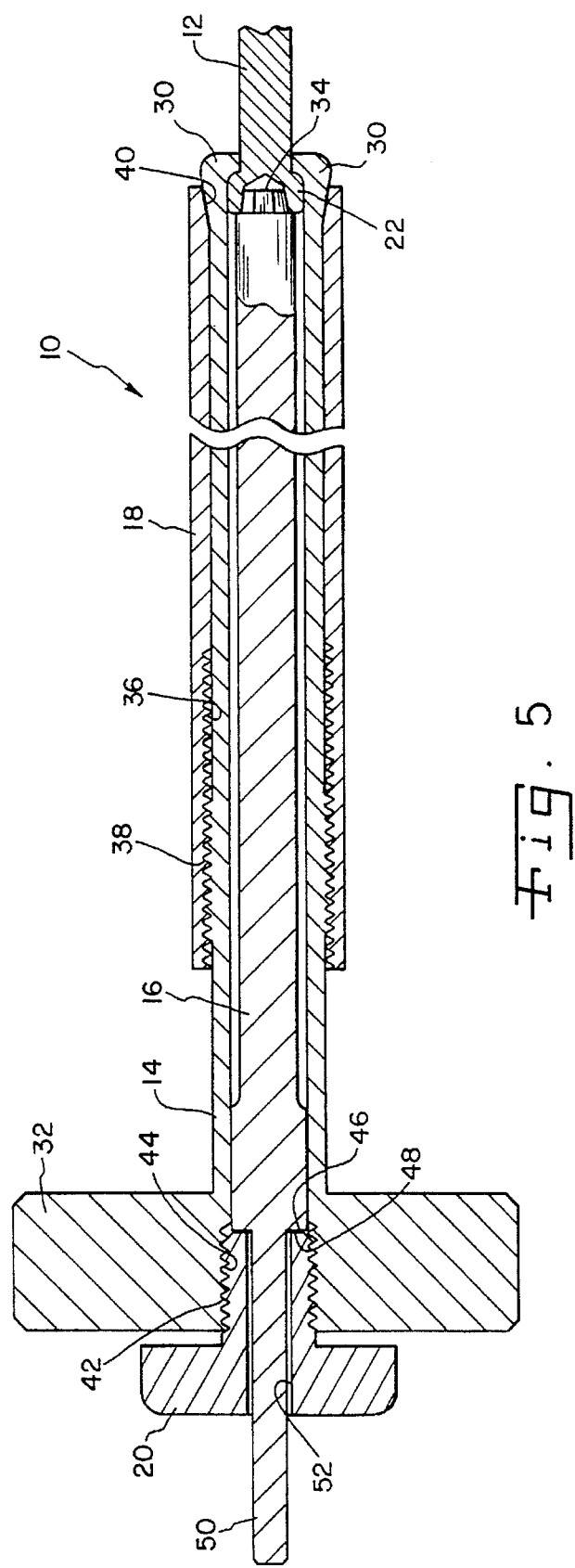

ORTHOPAEDIC APPARATUS FOR DRIVING AND/OR REMOVING A BONE SCREW

BACKGROUND OF THE INVENTION

1. Field of the Invention

The present invention relates to orthopaedic apparatus for driving and/or removing an orthopaedic screw, and, more particularly, to such orthopaedic apparatus which engage an enlarged head of a bone screw.

2. Description of the Related Art

Elongated fixation members used in orthopaedic applications, such as bone screws or pins, are typically used to fixate or stabilize a portion of a fractured bone relative to another portion of the bone. Known orthopaedic apparatus used to drive and/or remove bone screws or pins engage an end of the bone screw or pin in various ways. For example, some orthopaedic apparatus used to drive bone screws apply an axial force to the end of the bone screw. Illustrative of such apparatus are those disclosed by U.S. Pat. Nos. 4,901,712 (Voegeli et al.), 4,423,721 (Otte et al.), and 5,354,292 (Braeuer et al.).

Other orthopaedic apparatus used to drive or remove bone screws apply a radial or sideways force to the end of the bone screw. Illustrative of such apparatus are those disclosed by U.S. Pat. Nos. 4,140,111 (Morrill), 5,139,499 (Small et al.), 4,389,913 (Drouin et al.), and 4,911,154 (Vickers).

Still other orthopaedic apparatus used to drive or remove bone screws use a threaded interconnection between the apparatus and the bone screw. Illustrative of such apparatus are those disclosed by U.S. Pat. Nos. 3,334,624 (Schneider et al.), 4,963,144 (Huene), and 4,995,810 (Söderberg).

Moreover, it is also known to use an orthopaedic apparatus to remove a marrow nail by applying a collar or gripper jaws around a constricted portion of the head of the nail and using a self-tapping rod which threadingly engages the inner end of the hollow, marrow nail. While a securing ring holds the gripper jaws firmly against the constricted portion, it does not provide a radially inward gripping force to the nail. Such an apparatus is disclosed by U.S. Pat. No. 4,981,481 (Kranz et at.). An apparatus such as Kranz et al. could not be used with a bone screw because there is not enough depth in the recess of the head of a bone screw to allow the tapping operation of the apparatus rod.

What is needed in the art is an orthopaedic apparatus which allows reliable removal of an orthopaedic screw or pin.

SUMMARY OF THE INVENTION

The present invention provides an orthopaedic apparatus which applies both a radial and axial force to the enlarged head of a bone screw or pin, and thereby effectively locks the bone screw or pin relative to the orthopaedic apparatus.

The invention comprises, in one form thereof, an orthopaedic apparatus for at least one of removing and driving an elongated fixation member having an enlarged head. The orthopaedic apparatus includes a hollow, elongated body having an open end for receiving the enlarged head therein. The body further has a deflectable portion at the open end. A shaft is disposed within the body, and has a distal end disposed substantially adjacent to the body open end. The distal end has an exterior configuration which is adapted to mate with the enlarged head. The deflectable portion is configured to impart a radially inward force around the enlarged head and the shaft is configured to impart an axial compression force on the enlarged head, thereby locking the elongated fixation member relative to the orthopaedic apparatus.

An advantage of the present invention is that a bone screw having a stripped-out head can be reliably removed from a bone.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 1 is a side view of an embodiment of an orthopaedic apparatus of the present invention used to drive and/or remove a bone screw or pin;

FIG. 2 is an end view of the orthopaedic apparatus shown in FIG. 1, as viewed from the left of FIG. 1;

FIG. 3 is an end view of the orthopaedic apparatus shown in FIG. 1, as viewed from the right of FIG. 1;

FIG. 4 is a side, sectional view of the orthopaedic apparatus shown in FIGS. 1–3, with a bone screw positioned near the open end of the apparatus;

FIG. 5 is an enlarged side, sectional view of the orthopaedic apparatus shown in FIGS. 1–4, with a bone screw positioned within the open end of the apparatus; and FIG. 6 is an enlarged, fragmentary view of the distal end of the shaft of the orthopaedic apparatus shown in FIGS. 4 and 5.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Referring now to the drawings, there is shown an embodiment of an orthopaedic apparatus 10 which is used to remove and/or drive an elongated fixation member, such as a bone screw 12 (FIGS. 4 and 5). Bone screw 12 may be used, e.g., to attach or stabilize one portion of a fractured bone to another portion, or to attach another device, such as a bone plate (not shown) to a bone. Bone screw 12 includes an enlarged head 22 at one end thereof having a recess 24 adapted for receiving a tool, such as a portion of orthopaedic apparatus 10, therein. Recess 24, in the embodiment shown, has a hexagonal shape allowing the head of a hexagonal-shaped driver bit to be inserted therein. Enlarged head 22 may extend above the surface of the bone, and it is sometimes necessary to remove bone screw 12 from the bone by inserting the hexagonal driver bit into recess 24 of enlarged head 22. However, it is not uncommon for recess 24 to become stripped-out, whereby a conventional hexagonal-shaped driver bit is not by itself effective in removing bone screw 12 from the bone. Orthopaedic apparatus 10 allows a bone screw 12 having a stripped-out enlarged head 22 to be removed from a bone. Orthopaedic apparatus 10 generally includes a body 14, shaft 16 (FIGS. 4 and 5), sleeve 18 and thumb screw 20. Body 14, in the embodiment shown, is in the form of a hollow, elongated body having an open end 26 for receiving enlarged head 22 of bone screw 12 therein. Body 14 further has a deflectable portion 28 (FIG. 1) which may be deflected in a radially inward direction to provide a radially inward gripping force around enlarged head 22 of bone screw 12. More particularly, deflectable portion 28 includes a plurality of collet fingers 30 which are normally in the position shown in FIG. 4 when in a non-deflected position. Body 14 also includes a turn wheel 32 which provides increased rotational leverage for mining body 14.

Shaft 16 is disposed within body 14, and has a distal end 34 which is disposed substantially adjacent to open end 26 of body 14. Distal end 34 has an exterior configuration (FIGS. 3, 5, and 6) which is adapted to mate with recess 24 of enlarged head 22. More particularly, distal end 34 has a hexagonal exterior configuration which is adapted to be received within recess 24 and thereby engage bone screw 12. Of course, distal end 34 and recess 24 can be formed with other respective exterior and interior configurations which mate with each other.

Sleeve 18 is disposed about a portion of body 14, and is engaged with and movable in a longitudinal direction relative to body 14. More particularly, sleeve 18 includes internal threads 36 which are matingly engaged with exterior threads 38 formed on body 14. Rotation of sleeve 18 therefore causes movement of sleeve 18 in a longitudinal direction relative to body 14. Sleeve 18 may also include a chamfered surface 40 which approximately corresponds to the outwardly tapered exterior shape of collet fingers 30, as shown in FIG. 5. Sleeve 18 is configured to impart a radially inward force to collet fingers 30 when moved in a longitudinal direction toward open end 26.

Thumb screw 20 includes exterior threads 42 which engage interior threads 44 of turn wheel 32. Thumb screw 20 may be configured with a hexagonal shape, as shown in FIGS. 1 and 2, such that a wrench or the like can be engaged therewith and used to rotate thumb screw 20.

Thumb screw 20 also includes a shoulder 46 which is used to impart an axial compression force on an end face 48 of shaft 16. This axial compression mode is in turn transmitted to distal end 34, which applies an axial compression load to enlarged head 22 of bone screw 12.

A smaller diameter portion 50 extends from shaft 16 and through a central opening 52 formed in thumb screw 20. Prior to tightening thumb screw 20 against shaft 16, smaller diameter extending portion 50 allows shaft 16 to be manually rotated (as indicated by arrow 54) and manually longitudinally extended (as indicated by arrow 55) for alignment of distal end 34 with recess 24 in enlarged head 22 (FIG. 5).

Referring now to FIG. 6, details of distal end 34 are shown. More particularly, in the embodiment shown, distal end 34 has a hexagonal exterior configuration which is slightly tapered in a direction extending therefrom. Such a taper allows the respective edges thereof, such as indicated generally at 56, to in essence form cutting edges to cut into the periphery of a potentially stripped-out recess 24. The angle of the taper and length of cut are therefore preferably selected such that new edges may be cut into recess 24 if necessary. In the embodiment shown, distal end 34 has a taper of approximately between 10° to 15° relative to the longitudinal axis of shaft 16, as indicated by the angle $\alpha$ in FIG. 6. Preferably, the tapered end 34 is inserted into a non-tapered recess and is dimensioned to create an interference engagement with recess 24, thus cutting the new edges.

Referring to FIGS. 4 and 5, the use of orthopaedic apparatus 10 will now be described. Preliminarily, thumb screw 20 and sleeve 18 are both screwed toward an end of orthopaedic apparatus 10 which is opposite to open end 26 or screwed away from open end 26. This allows collet fingers 30 to move to the position shown in FIG. 4, and relieves any axial compression loading applied to shaft 16. Collet fingers 30 are spaced such that enlarged head 22 may be received therebetween. Next, bone screw 12 is placed into collet fingers 30 of body 14, and smaller diameter portion 50 of shaft 16 is manually rotated and longitudinally extended to position hexagonal distal end 34 into recess 24 of enlarged head 22. Sleeve 18 is then rotated and thereby moved in a longitudinal direction toward open end 26 to bias collet fingers 30 radially inward around enlarged head 22, as shown in FIG. 5. Alternatively, shaft 16 can be inserted into recess 24 after sleeve 18 is rotated toward open end 26 to bias collet fingers 30 around head 22. With hexagonal distal end 34 in place within enlarged head 22, thumb screw 20 is then tightened to engage shoulder 46 thereof against end face 48 of shaft 16. To that end, a wrench may be applied to thumb screw 20 for application of additional axial loading to end face 48. This axial loading is transferred to hexagonal distal end 34, and in turn to enlarged head 22 of bone screw 12. The combination of the radially inward force applied by collet fingers 30 and the axial compression loading applied by distal end 34 substantially locks bone screw 12 relative to orthopaedic apparatus 10. In the case of removing a screw 12 having a stripped out head, the screw may then be removed from the bone. It is noted that apparatus 10 may be utilized to remove or insert a bone screw or pin through a cannula (not shown) or a small incision.

The apparatus 10 may preferably be made from stainless steel, although any suitable materials may be utilized.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic apparatus for at least one of removing and driving an elongated fixation member having an enlarged head, said orthopaedic apparatus comprising:
   a hollow, elongated body having an open end for receiving the enlarged head therein, said body further having a deflectable portion at said open end; and
   a shaft disposed within said body, said shaft having a distal end disposed substantially adjacent to said body open end, said distal end having an exterior configuration adapted to mate with the enlarged head; and a thumb screw threadingly engaging said body at an end opposite said open end, said thumb screw configured to engage an end of said shaft and bias said shaft toward said body open end;
   whereby said deflectable portion is configured to impart a radially inward force around the enlarged head and said shaft is configured to impart an axial compression force on the enlarged head, thereby locking the elongated fixation member relative to said orthopaedic apparatus.

2. The orthopaedic apparatus of claim 1, wherein said deflectable portion comprises a plurality of collet fingers disposed at said open end, and further comprising a sleeve disposed about a portion of said body, said sleeve engaged with and movable in a longitudinal direction relative to said body, said sleeve configured to impart a radially inward force to said collet fingers when moved in a longitudinal direction relative to said open end.

3. The orthopaedic apparatus of claim 2, wherein said sleeve includes interior threads and said body includes exterior threads, said sleeve interior threads being engaged with said body exterior threads.

4. The orthopaedic apparatus of claim 1, wherein the elongated fixation member comprises a bone screw.

5. The orthopaedic apparatus of claim 1, wherein said shaft distal end has a hexagonal exterior configuration.

6. The orthopaedic apparatus of claim 5, wherein said hexagonal exterior configuration is slightly tapered from said distal end.

7. The orthopaedic apparatus of claim 6, wherein said slightly tapered distal end comprises a taper of approximately between 10° to 15°.

8. The orthopaedic apparatus of claim 1, wherein said thumb screw includes a central opening, said shaft including a smaller diameter portion which extends through said central opening, said smaller diameter portion allowing said shaft to be manually positioned for alignment and engagement of said shaft distal end with the enlarged head.

9. The orthopaedic apparatus of claim 1, wherein said body further comprises a turn wheel providing increased rotational leverage for turning said body.

10. An orthopaedic apparatus for at least one of removing and driving an elongated fixation member having an enlarged head, said orthopaedic apparatus comprising:

a hollow, elongated body having an open end for receiving the enlarged head therein, said body further including a plurality of collet fingers disposed at said open end;

a sleeve disposed about a portion of said body, said sleeve engaged with and movable in a longitudinal direction relative to said body, said sleeve configured to impart a radially inward force to said collet fingers when moved in a longitudinal direction relative to said open end;

a shaft disposed within said body, said shaft having a distal end disposed substantially adjacent to said body open end, said distal end having an exterior configuration adapted to mate with the enlarged head; and means for biasing said shaft toward said body open end, wherein said biasing means comprises a thumb screw threadingly engaging said body at an end opposite said open end, said thumb screw configured to engage an end of said shaft opposite said distal end.

* * * * *